United States Patent [19]

Csoknyai et al.

[11] Patent Number: 5,557,112
[45] Date of Patent: Sep. 17, 1996

[54] DUAL RADIATION ULTRAVIOLET LAMP

[75] Inventors: George Csoknyai, Orange, Conn.; Arpad L. Pirovic, Montvale, N.J.

[73] Assignee: Light Sources, Inc., Milford, Conn.

[21] Appl. No.: 505,605

[22] Filed: Jul. 21, 1995

[51] Int. Cl.⁶ .............................. A61N 5/06; H01J 61/48
[52] U.S. Cl. .................... 250/504 R; 250/494.1; 607/94; 313/487
[58] Field of Search ............... 250/504 R, 494.1, 250/493.1; 607/94; 313/487, 488

[56] References Cited

U.S. PATENT DOCUMENTS

| | | |
|---|---|---|
| 750,554 | 1/1904 | Potter . |
| 1,792,347 | 2/1931 | Zecher . |
| 2,916,645 | 12/1959 | Lemmers et al. ............ 313/493 |
| 3,767,956 | 10/1973 | Bauer ............................ 313/109 |
| 4,194,125 | 3/1980 | Wolff ............................ 250/504 |
| 4,652,790 | 3/1987 | Wood ............................ 313/112 |
| 4,703,184 | 10/1987 | Wolff ............................ 250/504 R |
| 4,959,551 | 9/1990 | Schlitt ........................... 250/504 R |
| 4,967,090 | 10/1990 | Schlitt ........................... 250/504 R |
| 5,008,789 | 4/1991 | Arai et al. ..................... 362/255 |
| 5,216,323 | 6/1993 | Baaten et al. ................. 313/487 |

*Primary Examiner*—Jack I. Berman
*Attorney, Agent, or Firm*—Pepe & Hazard

[57] ABSTRACT

A fluorescent lamp having multiple zones with different ultraviolet radiation characteristics along its length has a tube with a first fluorescent coating for producing ultraviolet radiation of substantially uniform intensity extending over a first finite length of the tube adjacent one end. A second fluorescent coating extending over a second finite length of the tube adjacent its other end thereof produces ultraviolet radiation of a substantially uniform intensity and having radiation characteristics which are different from those produced in the first finite length. Generally, the UVB intensity and UVB/UVA ratio will be increased. This lamp is ideally suited for use in tanning chambers to provide uniform tanning by providing a higher intensity and a higher UVB/UVA ratio for radiation in the area of the head.

14 Claims, 2 Drawing Sheets

DUAL RADIATION ULTRAVIOLET LAMP

BACKGROUND OF THE INVENTION present invention relates generally to fluorescent lamps, and more particularly to ultraviolet fluorescent lamps providing different ultraviolet radiation characteristics adjacent one end.

As is well known, tanning is the result of the body's reaction to exposure to ultraviolet radiation. Tanning can provide protection against the sun's rays, and it may also serve a cosmetic function in that many people desire to exhibit the healthiness represented by a desirable tanned appearance.

As a result, tanning salons are becoming very popular, and tanning lamps are also purchased for home and club use. Many devices have been developed to make tanning with the use of artificial illumination sources more enjoyable and efficient. Generally, tanning salons use a booth, chamber, or bed, in or on which a person is placed for exposure to ultraviolet tanning radiation from a number of lamps. Generally, the tanning bed or chamber has a multiplicity of fluorescent lamps that extend longitudinally along the length of the individual and disposed in a parallel array of a width which will uniformly expose the full width of the body. Typically, these lamps are approximately six feet long, or the height of an individual.

Most ultraviolet tanning fluorescent lamps have been uniformly coated with a fluorescent material to provide a uniform radiation intensity over the length, and as many as "several dozen" lamps may be used in a single bed or chamber.

It has been recognized that, in most individuals, the facial area may require different ultraviolet radiation characteristics than the radiation area provided to the body in order to obtain the desired uniform tanning effect. In part, this may be due to higher levels of melanin in the skin in the facial area due to its greater exposure to the sun.

Merely increasing the intensity of the ultraviolet radiation may provide increased tanning effect, but an ideal approach to providing increased tanning effect in an area of the body would involve altering not only increasing intensity but also increasing the ratio of UVB to UVA rays so that greater melanin production is stimulated.

As is also well known, shorter wave ultraviolet light of 260–320 nanometers (UVB) stimulates the production of the pigment melanin by the melanocytes in the skin. Once the melanin has been produced, the longer wavelength ultraviolet light of 320–400 nanometers (UVA) darkens or oxidizes the melanin granules which are produced and thereby generates the tanning effect. Thus, in most effective tanning lamps there is present in the radiation both UVB and UVA rays with the UVB rays stimulating the production of melanin which migrates upwardly towards the horny layer or corneum of the skin where the UVA then oxidizes the melanin to produce the tanning effect. The UVB radiation is also desirable from the standpoint of producing a thickening of the skin to provide protection from excessive radiation. To remedy this, some tanning beds or chambers also use metal halide lamps in the area of the head to provide increased radiation to the facial area. Still others interpose relatively short lamps between the longer lamps to provide desired additional intensity or characteristics for the radiation in the facial area. In this way, the overall duration of time spent in the tanning bed or chamber is held constant while the ultraviolet radiation is increased in intensity or varied in its spectral characteristics in the facial area of the individual to provide the desired uniform tanning over the entire body. Although these composite tanning beds or chambers may provide the desired uniform tanning effect, they are more complicated to fabricate and maintain, and they are relatively expensive.

A lamp which will provide different radiation characteristics Schlitt U.S. Pat. No. 4,967,090 granted Oct. 30, 1990 attempts to provide different spectral characteristics in a single lamp by applying different phosphor coatings to discrete circumferential portions of the lamp. Thus, his lamp may be rotated to change the UVB/UVA characteristics rather than by providing different lamps with uniform characteristics.

It is an object of the present invention to provide a novel ultraviolet lamp that has a portion adjacent one end thereof providing ultraviolet rays of different characteristics than those over the remainder of the lamp.

It is also an object to provide such a lamp which may be fabricated relatively easily and economically, and which will exhibit a relatively long life.

Another object is to provide a tanning bed or chamber which is of relatively simple construction using only these novel lamps so that it can be easily and inexpensively manufactured and maintained, while providing the desired tanning effect by generating different radiation characteristics over the facial area of the individual.

SUMMARY OF THE INVENTION

It has now been found that the foregoing and related objects may be readily attained in a fluorescent lamp having multiple zones with different ultraviolet radiation characteristics along its length comprising a tube with a first fluorescent coating on its interior of the tube adapted to produce ultraviolet radiation of substantially uniform characteristics and extending over a first finite length of the tube adjacent one end thereof. A second fluorescent coating is provided on the interior of the tube and extends over a second finite length of the tube adjacent the other end for producing ultraviolet radiation of a substantially uniform characteristics which are different than those of the radiation produced in the first finite length.

Preferably, the intensity of UVB radiation produced in the second finite length is ten to fifty percent greater than the intensity of radiation produced in the first finite length, and the UVB/UVA ratio of the radiation in the second finite length is also increased. The second finite length is about 8–18 inches.

The fluorescent coatings may comprise mixtures of fluorescent coating materials having different radiation characteristics, and the proportions may be varied to produce the variations in intensity and UVB/UVA ration desired (collectively "spectral energy distribution"). One of the coatings also desirably includes a material fluorescing in a visible wavelength of light to provide a coloration distinct from that of the light produced by the other coating. If so desired, each of the coatings may include a material fluorescing in visible wavelengths, but fluorescing at different wavelengths.

A fluorescent tanning lamp assembly for a tanning chamber will comprise an array of a multiplicity of parallel spaced elongated lamps each having multiple discrete zones levels of different radiation characteristics along its length as heretofore described.

DETAILED DESCRIPTION OF THE PREFERRED EMBODIMENT

Figure 1:
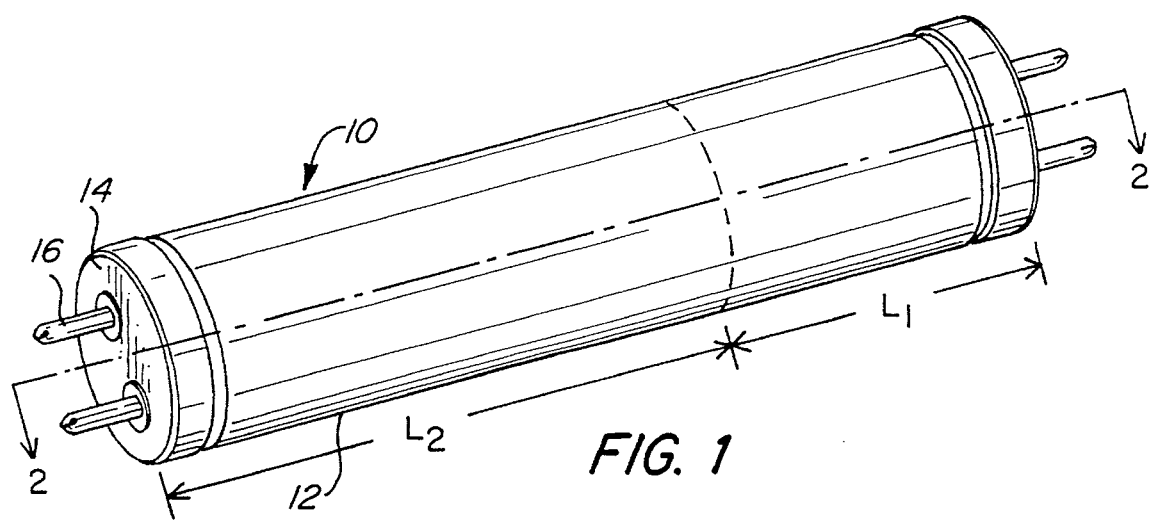
FIG. 1 is a perspective view of a fluorescent lamp embodying the present invention.
Figure 2:
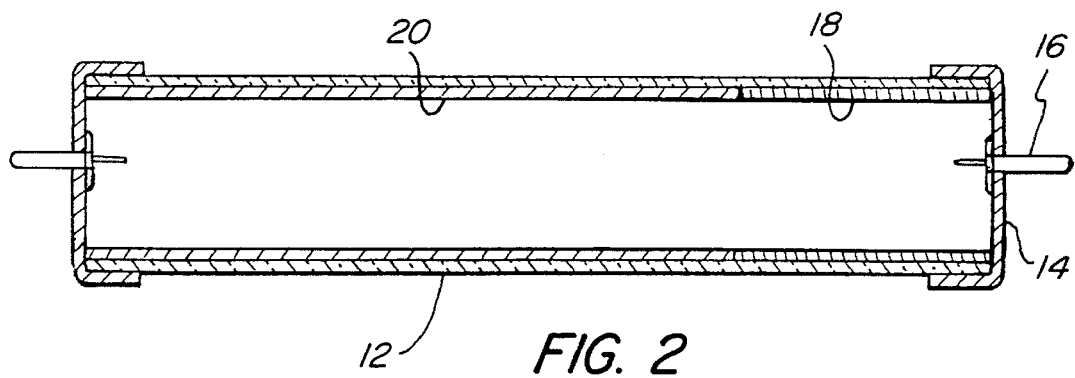
FIG. 2 is a longitudinal cross section taken along the line 2—2 of FIG. 1.

FIGS. 1 and 2 generally illustrate an ultraviolet fluorescent lamp 10 embodying the present invention and including an elongated tubular glass envelope or tube with end caps 14 at each end. Electrode pins or contacts 16 extend through the caps. On the inner surface of the tube 12 adjacent one end is a first fluorescent coating 18 which extends for a distance $L_1$ about 10–18 inches, and this coating will generate ultraviolet radiation of a higher intensity and relatively high UVB/UVA ratio. A second fluorescent coating 20 extends over the remainder $L_2$ of the length of the tube 12, and it will generate ultraviolet radiation of a lower intensity and a lower UVB/UVA ratio.

The first fluorescent coating 18 will generally have a UVB radiation intensity, and accordingly a tanning strength, approximately 10%–50% greater than the intensity, and, accordingly, the tanning strength of the second lower intensity fluorescent coating 20. The UVB/UVA ratio is 5–60 percent greater in the first coating.

Because the UV radiation is not in the visible spectrum and the lamp produces two intensities of ultraviolet radiation, the addition of fluorescent material fluorescing in the visible color spectrum to at least one the coatings will produce radiation in the visible spectrum as it is projected onto the individual in the tanning chamber or bed. As a result, the individual can position his or her facial area to receive the desired higher tanning strength produced by the higher UVB content produced by the fluorescent coating 18. Fluorescent materials providing different visible colors may be used in both coatings, or one of the coatings 20, 22 may have no visible color fluorescing material and a differentiation will still be apparent between the two intensity zones.

The different fluorescent coatings 18, 20 producing different ultraviolet spectral energy distribution or tanning strengths are easily obtained by mixing known fluorescent materials generating different radiation intensities to provide coatings which produce the desired intensity of radiation. Philips U-214 sold by Philips-Elmet of Lewiston, Me. is a well known fluorescent phosphor coating material for producing UV radiation as is Nichia NP 806 sold by Nichia America Corporation of Lancaster, Pa. These two well known UV producing fluorescent phosphor materials may be mixed in different proportions to produce the desired UV radiation ratio and intensity, and therefore predetermined tanning strengths.

One of many possibilities is the following specific example, these two UV fluorescent coating materials can be mixed in a ratio of 90:10 to provide a higher intensity fluorescent coating having radiation with a UVB/UVA ratio of 0.066 and radiation levels of 2.1 (UVA) and 0.14 (UVB) microwatts/cm$^2$. When mixed in a ratio of 93:1 to provide a lower intensity, the UVB/UVA ratio is reduced to 0.0385 and the radiation levels are 2.2 (UVA) and 0.085 (UVB) microwatts/cm$^2$. To provide a visible coloration differential, the lower UVB radiation intensity coating may also contain 6% by weight of a red fluorescing material such as NP 340 sold by Nichia America. In this case the high intensity radiation will exhibit the bluish tint characteristic of the one end of the ultraviolet wavelength, and the lower intensity radiation will have a readily visible red coloration.

In another combination, the lower intensity coating includes 93 parts of the Phillips U-214, 5 parts of the Nichia NP 806 and 2 parts of the Nichia NP 340. In this instance, the UVB/UVA ratio of the lower intensity coating is 0.052, and its radiation levels are 2.10 (UVA) and 0.12 (UVB) microwatts/cm$^2$.

It is also possible to use distinct single ultraviolet fluorescent component coatings depending upon the desired UVA/UVB ratios and the availability from manufacturers.

The high intensity fluorescent coating conveniently provides the coating 18 in that portion of the lamp 10 positioned over the face area of an individual in a tanning chamber so that the desired increased radiation intensity is provided over the face portion of the individual to produce the desired tanning effect.

Figure 3:
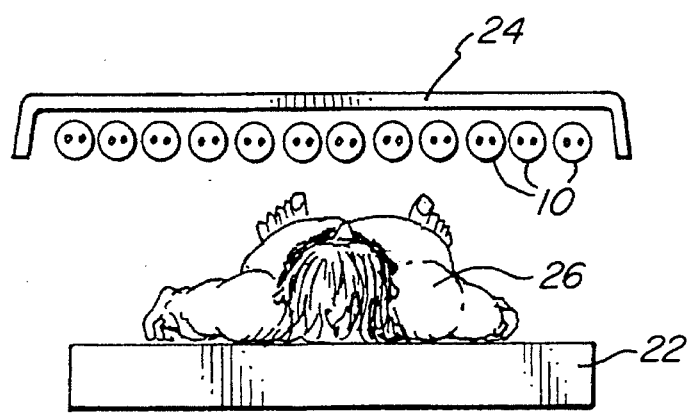
FIG. 3 is an end view of an array of lamps embodying the present invention adapted to be employed in a tanning chamber.

As is conventional in tanning chambers and as indicated in FIG. 3, an array of the lamps 10 generally extends longitudinally along the length of the individual. Since the distance $L_1$ for the high intensity portion 18 is between approximately 12 and 18 inches, or approximately 30 cm to 46 cm, a six foot (or 1.83 meter) lamp will have a distance $L_2$ of 54–60 inches or approximately 137–152/cm.

The wavelength of the ultraviolet radiation produced by the fluorescent tanning lamp 10 is preferably in a range in the middle ultraviolet region, i.e., 260–400 nanometers.

As seen in FIG. 3, a multiplicity of parallel extending lamps 10 (generally 15–36) is used to provide an array of a width sufficient to provide a uniform intensity across the width of the person 26 in a tanning chamber 22, and generally they are closely spaced. A reflector 24 may be provided about the array to increase the efficiency of radiation by redirecting the light exiting the upper side of the lamps 10 towards the user. Alternatively, and if so desired, a reflective coating may be provided over a portion of the periphery of the tube so as to redirect the radiation, but it should be uniform over the length of the lamp.

Figure 4:
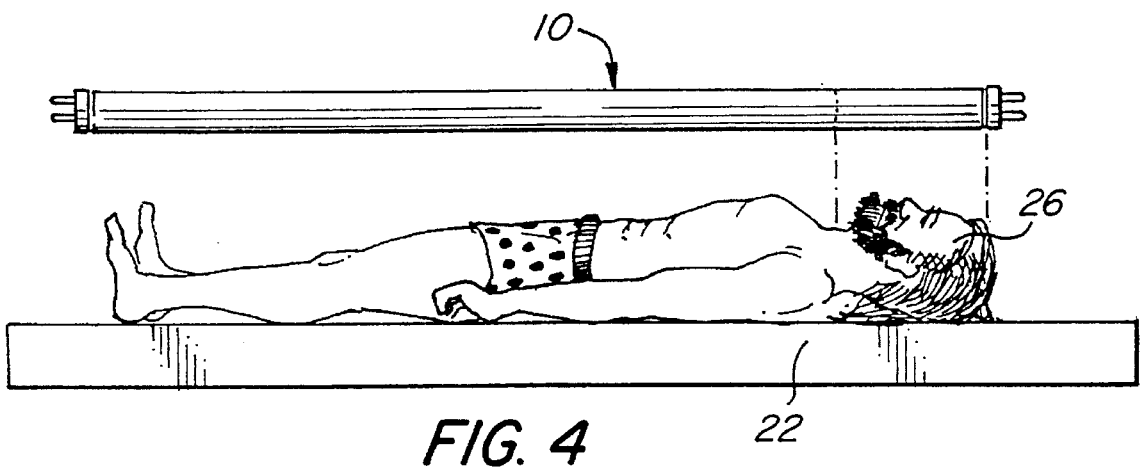
FIG. 4 is a side elevational view of an individual in a tanning chamber employing the lamps of the present invention.

As seen in FIG. 4, an individual 26 is lying in a tanning chamber 22. The fluorescent lamps 10 of the array are positioned over the individual 42 so that the ultraviolet radiation produced by the higher tanning strength fluorescent coating 18 in the zone $L_1$ covers the head and neck of the individual while the lower intensity ultraviolet radiation produced by the lower tanning strength fluorescent coating 20 in the zone $L_2$ extends from the neck to the feet. This produces the desired tanning effect in the facial area which will normally require radiation of greater intensity because of the higher melanin level in the skin. When one (or both) of the fluorescent coatings contains a differentially visible fluorescent material, the change in visible color illumination will permit the individual 26 to be more precisely positioned in the tanning bed or chamber 22.

Thus, it can be seen from the foregoing detailed description and attached drawings that the ultraviolet lamp of the present invention produces controlled radiation of different characteristics along its axial length. The radiation may also be provided with differential visible coloration if so desired. The lamps may be fabricated readily and relatively economically and will exhibit relatively long life. An array of the novel lamps provides a tanning chamber in which the head region may be exposed to radiation of higher intensity than that over the remainder of the body to provide a uniform tanning effect.

Having thus described the invention, what is claimed is:

1. A fluorescent lamp having multiple zones with different ultraviolet radiation characteristics along its length comprising:

(a) a tube;

(b) a first fluorescent coating on the interior of said tube adapted to produce ultraviolet radiation of substantially uniform intensity and extending over a first finite length of said tube adjacent one end thereof; and (c) a second fluorescent coating on the interior of said tube extending over a second finite length of said tube adjacent the other end thereof for producing ultraviolet radiation of a substantially uniform intensity and having radiation characteristics different from those of the radiation produced in said first finite length.

2. The fluorescent lamp in accordance with claim 1 wherein the UVB intensity of radiation produced in said second finite length is ten to fifty percent greater than the UVB intensity of radiation produced in said first finite length and wherein the UVB/UVA ratio is also greater.

3. The fluorescent lamp in accordance with claim 1 wherein said second finite length is about 8–18 inches.

4. The fluorescent lamp in accordance with claim 1 wherein said fluorescent coatings comprise mixtures of fluorescent coating materials in which the proportions are varied to produce the variation in radiation characteristics.

5. The fluorescent lamp in accordance with claim 1 wherein one of said coatings also includes a material fluorescing in a visible wavelength of light providing a coloration distinct from that of the light in the other of said coatings.

6. The fluorescent lamp in accordance with claim 5 wherein each of said coatings also includes a material fluorescing in a visible wavelength, said material in said first coating providing a first coloration and that in said second coating providing a second distinct coloration.

7. A fluorescent tanning lamp having multiple zones with different ultraviolet characteristics along its length comprising:

(a) a tube;

(b) a first fluorescent coating on the interior of said tube along a first finite length adjacent one end of said tube, said coating being adapted to produce ultraviolet radiation of substantially uniform intensity; and (c) a second fluorescent coating along a second finite length of about 8–18 inches of said tube adjacent the other end of said tube adapted to provide an increased UVB intensity of radiation emanating from the said second finite length, the UVB intensity of radiation emanating in said second finite length is ten to fifty percent greater than the UVB intensity of the radiation in said first finite length and wherein the UVB/UVA ratio is also larger.

8. The fluorescent lamp in accordance with claim 7 wherein said fluorescent coatings comprise mixtures of fluorescent coating materials in which the proportions are varied to produce the variation in radiation characteristics.

9. The fluorescent lamp in accordance with claim 7 wherein one of said coatings also includes a material fluorescing in a visible wavelength of light providing a coloration distinct from that of the light in the other of said coatings.

10. A fluorescent tanning lamp assembly for a tanning chamber comprising an array of a multiplicity of parallel spaced elongated lamps having multiple zones with different ultraviolet characteristics of radiation along their length and each comprising:

(a) a tube;

(b) a first fluorescent coating on the interior of said tube adapted to produce ultraviolet radiation of substantially uniform intensity and extending over a first finite length of said tube adjacent one end thereof; and (c) a second fluorescent coating on the interior of said tube extending over a second finite length of said tube adjacent the other end thereof for producing ultraviolet radiation of a substantially uniform intensity and having radiation characteristics different from those of the radiation produced in said first finite length.

11. The fluorescent tanning lamp assembly in accordance with claim 10 wherein the intensity of UVB radiation emanating in said second finite length is ten to fifty percent greater than the intensity of UVB radiation in said first finite length and wherein the UVB/UVA ratio is also greater.

12. The fluorescent tanning lamp assembly in accordance with 10 wherein said second finite length is about 8–18 inches.

13. The fluorescent tanning lamp assembly in accordance with 10 wherein said fluorescent coatings comprise mixtures of fluorescent coating materials in which the proportions are varied to produce the variation in radiation characteristics.

14. The fluorescent tanning lamp assembly in accordance with claim 10 wherein one of said coatings also includes a material fluorescing in a visible wavelength of light providing a coloration distinct from that of the light in the other of said coatings.

* * * * *